United States Patent [19]

Christensen

[11] Patent Number: Plant 6,796

[45] Date of Patent: May 9, 1989

[54] HYBRID TEA ROSE PLANT CV. AROKISH

[75] Inventor: Jack E. Christensen, Ontario, Calif.

[73] Assignee: Bear Creek Gardens, Medford, Oreg.

[21] Appl. No.: 132,575

[22] Filed: Dec. 14, 1987

[51] Int. Cl.[4] ..... A01H 5/00

[52] U.S. Cl. ..... Plt./14

[58] Field of Search ..... Plt./14

*Primary Examiner*—Robert E. Bagwill

*Attorney, Agent, or Firm*—Majestic, Parsons, Siebert & Hsue

[57] ABSTRACT

This invention relates to a new and distinct variety of hybrid tea rose plant cv. Arokish, particularly suited for garden decoration, identified by its pure white flowers of large size having a strong, penetrating fruity fragrance.

1 Drawing Sheet

The present invention relates to a new and distinct variety (cv. Arokish) of rose plant of the hybrid tea class. The plant is a bushy outdoor seedling cultivated for garden decoration. It was first originated by Jack E. Christensen in Ontario, Calif., U.S.A. under conditions of careful control and observation, and has as its seed parent the floribunda rose, Deep Purple (U.S. Plant Pat. No. 4,672), and as its pollen parent, an unnamed rose seedling selected from the progeny of the cross fertilization between the hybrid tea rose, Ivory Tower (U.S. Plant Pat. No. 4,658) and the floribunda rose, Angel Face (U.S. Plant Pat. No. 2,792).

The new rose cv. Arokish is particularly distinguishable from other commercialized rose cultivars by the following combination of characteristics: its vigorous, upright, and strong growing plants; its very freely blooming, pure white flowers of large size, borne on medium to long strong stems; and the strong and penetrating fruity fragrance of its flowers.

Arokish holds its distinguishing characteristics through succeeding propagations by budding and cuttings.

The new variety cv. Arokish may be distinguished from its seed parent, Deep Purple, by the following combination of characteristics: Whereas Deep Purple is a floribunda rose, Arokish is a hybrid tea rose. The petal color of Arokish is white, whereas the petal color of Deep Purple is a mauve-pink.

The new variety may be distinguished from its pollen parent, an unnamed seedling (Ivory Tower x Angel Face), by the following combination of characteristics: Whereas the flower color of the pollen parent is lavender, the flower color of Arokish is white. Whereas the flower fragrance of the pollen parent is strong and citrus-like, the flower fragrance of Arokish is strong, penetrating and fruity, although not quite as strong as the flower fragrance of the pollen parent. Arokish is more vigorous and stronger growing than its pollen parent.

The accompanying drawing illustrates the new variety in color as grown in Somis, Calif., and shows the flowering thereof from bud to full bloom.

The descriptive matter which follows pertains to roses of the new variety grown outdoors in Somis, Calif., and is believed generally to apply to plants grown under similar conditions of soil and climate elsewhere. Plants and flowers of the new variety grown in other locations may vary in slight detail according to the climatic, soil and cultural conditions under which the variety is grown.

Throughout this specification, color names beginning with a small letter signify that the name of that color as used in common speech is aptly descriptive. Color names beginning with a capital letter designate values based upon the R.H.S. Colour Chart of The Royal Horticultural Society of London, England.

FLOWER

The new variety usually bears a single flower per stem. Flowers are sometimes borne two to three per stem, in irregular clusters. Flower stems are of average strength to strong for the class. A few flower stems are weak. Flower stems are of medium length to long for the class. Outdoors, the plant blooms very freely and continuously during the growing season. Flowers have a strong and penetrating fruity fragrance.

BUD

The peduncle is of average length for the class, of average caliper, strong and erect. The peduncle is mostly smooth with some stipitate glands. Bud color is near Yellow-Green 146C.

Before the calyx breaks, the bud is average in size for the class, of average length, and ovoid in form with a conspicuous neck. There are a few stipulate glands and a glandular bloom on the surface of the bud. The bud lacks foliaceous parts which extend beyond the tip of the bud.

As the calyx breaks, petals ar near White 155B in color; sepal color is near Green 146B.

The inner surface of the sepals is lined with a fine wooly tomentum. Sepal margins are lined with stipitate glands.

As the first petal opens, buds are average in size for the class, long and urn-shaped. The color of the outside of the bud petals is near White 155A. The inner surface of the bud petals is near Yellow-White 158B in color.

The bud opens up well and is not prevented from opening by cold, hot, wet or dry weather.

BLOOM

The size of the bloom when fully open is average for the class, about 3½ to about 4 inches in diameter. Petalage is very double, averaging from about 32 to about 34 petals arranged regularly, plus 2 to 5 petaloids.

At one half open, blooms are somewhat high centered to flat-topped in form, with petals cupped and petal edges somewhat reflexed outward.

When fully open, the blooms are cupped, with petals more cupped and petal edges moderately reflexed outward.

The petals are of heavy substance, of average thickness, satiny on the inside surface and slightly satiny on the outside surface. Outside petals are nearly round in shape, sometimes scalloped, with rounded apices bearing 1 to 2 notches. Intermediate petals are nearly round to slightly obovate in shape with rounded apices bearing zero to one notch. Inside petals are obovate with rounded apices usually bearing zero to one notch.

Petal colors may be modified by being washed with other colors.

The following paragraph describes the color values observed in a newly opened flower from a plant of the new variety grown outdoors in Somis, Calif. in November of 1987.

The color of the outside and inside surface of the outside and intermediate petals is almost totally white, near White 155B in color, with slight greenish tints of near Green White 157C near the basal attachment zone. The color of the outside and inside surface of the inner petals is near Yellow-White 158D.

The folowing paragraph describes the color values observed in a flower open for three days outdoors from a plant of the new variety in November, 1987 at Somis, Calif.

The color of the outside surface of the outside petals is a white, slightly tinted with green, near Green-White 157D. The color of the inside surface of the outside petals is near White 155D. The color of the outside and inside surface of the inside petal is a warm, yellow-tinted white, near White 158D, blending into near White 155D at the top half of the petal.

The general color effect of the newly opened flower is almost a pure white, near White 155D, with a warm, very light yellow tint near Yellow-White 158D.

After being open three days, the general color effect of the flower is very near that of the newly opened flower with a slightly greater yellow tint.

Petals usually persist and are not particularly affected by cold, hot, wet or dry weather.

Flowers grown in the month of September last from 3 to 4 days on a bush in the garden. Cut flowers from rose plants grown outdoors in September last from 5 to 6 days when kept at living room temperatures.

REPRODUCTIVE ORGANS

Stamens are many in number and are arranged irregularly about the pistils; a few may also be mixed with petaloids. Filaments are short to average in length and many have medium to large sized anthers. Anthers open approximately all at once. Mature and immature anthers are near Yellow-Orange 20B in color. Pollen is produced in sparse to moderate quantities and is near Yellow-Orange 20B in color.

Pistils are average in number for the class (about 30). Styles are uneven, short to average in length, of thin to average caliper, and are somewhat bunched. Stigma color is near Yellow-Orange 20B. Most ovaries are enclosed in the calyx and a few protrude from the calyx.

Hips are of average length, oblong in form and smooth, with thick, fleshy walls. Hips are near Orange-Red 31A in color.

Sepals are permanent, of average length and curled. The inside surface of the sepals is near Brown 200A; the outside surface of the sepals is near Brown 200B in color.

Seeds are produced in average quantities, about 20 to 30 in number.

FOLIAGE

The compound leaves comprise 5 to 7 leaflets. Leaves are borne in average to abundant quantities and are average to large in size for the class. Leaves are moderately heavy and are non-glossy. Leaflets are oval to ovate in shape, with acute apices; their bases are round and their margins are simply serrate.

The color of the upper surface of mature leaves is near Yellow-Green 147A. The under surface of the mature leaves is near Yellow-Green 147C in color. The upper surface of the young leaves is near Yellow-Green 147A in color, tinted with near Red-Purple 59D. The under surface of young leaves is near Yellow-Green 147C in color, tinted with near Red-Purple 59D.

The rachis is average in size. Its upper side bears some stipitate glands on the edges. The underside is sparsly prickly.

Stipules are short and moderately narrow, having very short points turning out at an angle of more than 45° and are slightly recurved toward the stem.

Plants of the new variety are average in their resistance to mildew and blackspot as compared with other cultivars now in commerce when grown under comparable conditions at Somis, Calif.

GROWTH

Plants of the new variety are average in height, upright, bushy and much branched in habit. Plant growth is vigorous. Canes are of average caliper for the class. The main stems are near Yellow-Green 144A in color. They bear many large thorns which are average in length for the class, almost straight and hooked slightly downward. The thorn base is moderately short and moderately narrow. Large thorns are near Greyed-Brown 199B in color. There are no small prickles and no hairs.

Branches are near Green 137B in color; they bear several large thorns of average-length for the class. Large thorns are hooked slightly downward and have narrow bases of average length. Large thorns are near Greyed-Red 181D in color. There are no small prickles and no hairs.

New shoots are near Greyed-Red 181D in color. New shoots bear several large thorns which are moderately short to average in length for the class. Large thorns are almost straight to hooked slightly downward and have short, narrow bases. Large thorns are near Greyed-Red 181D in color. There are no small prickles and no hairs.

I claim:

1. A new and distinct variety of hybrid tea rose plant cv. Arokish, and the parts thereof, being particularly characterized by its vigorous, upright and strong growing plants; its very freely blooming, pure white flowers of large size, borne on medium to long strong stems; and the strong and penetrating fruity fragrance of its flowers, substantially as described and illustrated herein.

* * * * *

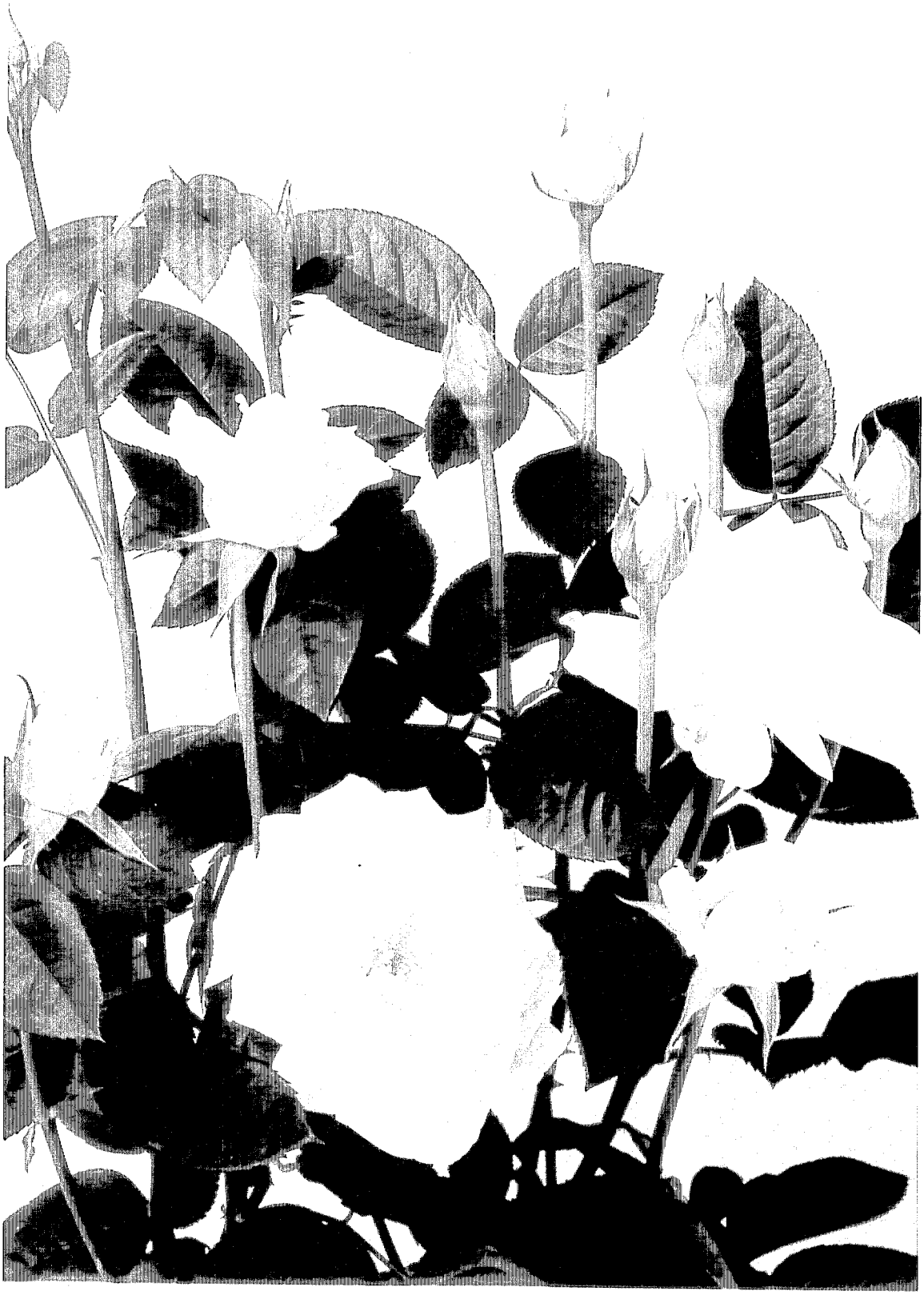

UNITED STATES PATENT AND TRADEMARK OFFICE

CERTIFICATE OF CORRECTION

PATENT NO. : Plant 6,796

DATED : May 9, 1989

INVENTOR(S) : Christensen

It is certified that error appears in the above-identified patent and that said Letters Patent is hereby corrected as shown below:

Col. 4, line 27: "sparsly" should be --sparsely--.

Signed and Sealed this

Fifth Day of December, 1989

*Attest:*

JEFFREY M. SAMUELS

*Attesting Officer*

*Acting Commissioner of Patents and Trademarks*